United States Patent [19]

Bratthäll

[11] 4,044,605
[45] Aug. 30, 1977

[54] APPARATUS FOR MEASURING FOULING ON THE INSIDE OF A HEAT-EXCHANGER TUBE

[75] Inventor: Lars Bratthäll, Linkoping, Sweden

[73] Assignee: Stal-Laval Apparat AB, Linkoping, Sweden

[21] Appl. No.: 630,946

[22] Filed: Nov. 12, 1975

[30] Foreign Application Priority Data

Nov. 15, 1974 Sweden .............................. 7414392

[51] Int. Cl.² ......................................... G01N 25/18
[52] U.S. Cl. ....................................... 73/61.2; 73/61.3; 165/11
[58] Field of Search ..................... 73/15 R, 61.2, 61.3, 73/112, 432 R; 165/11

[56] References Cited

U.S. PATENT DOCUMENTS

| | | | |
|---|---|---|---|
| 1,217,074 | 2/1917 | Scanes | 73/112 |
| 2,858,113 | 10/1958 | Miller | 165/11 X |
| 3,312,274 | 4/1967 | Sebald | 165/11 X |
| 3,552,189 | 1/1971 | Courvoisier et al. | 73/61.2 |
| 3,643,541 | 6/1953 | McCreary | 73/432 A X |

*Primary Examiner*—Richard C. Queisser
*Assistant Examiner*—John S. Appleman

*Attorney, Agent, or Firm*—Kenyon & Kenyon, Reilly, Carr & Chapin

[57] ABSTRACT

The apparatus comprises a test tube having substantially the same composition as the heat-exchanger tube suspected as fouling internally. A pressure chamber encloses this test tube and forms a space around the test tube and isolated from external influences. This pressure chamber has means for filling the space around the test tube with a vapor that condenses to liquid on the outside of the test tube, the pressure in the pressure chamber being dependent on whether or not or the degree the vapor condenses to liquid on the test tube. Means are provided for measuring the fluid pressure on the inside of the pressure chamber, this means providing a measure of the heat exchange between the vapor and any medium flowing inside of the test tube. Therefore, by connecting this apparatus so that the medium flowing through the heat-exchanger tube is shunted, in part, through the test tube of this apparatus, the apparatus provides a measure of fouling occurring inside of the heat-exchanger tube because substantially the same fouling occurs inside of the test tube of this apparatus, the degree of which can be continuously monitored by observation or automatic recording of the fluid pressure in the pressure chamber of the apparatus.

4 Claims, 2 Drawing Figures

APPARATUS FOR MEASURING FOULING ON THE INSIDE OF A HEAT-EXCHANGER TUBE

BACKGROUND OF THE INVENTION

There are heat exchangers comprising a casing surrounding a bundle of tubes through which a primary medium is flowed, a secondary medium being flowed through the casing surrounding the bundle of tubes for either heating or cooling by the medium flowing through the tubes of the tube bundle.

Often the primary medium flowed through the tubes of the tube bundle, is capable of fouling the insides of the tubes of the tube bundle, with time. The primary medium may be obtained from industrial waste water, public waterways and the like, and the fouling occurring on the insides of the tube bundle may be either mechanical deposits of sediment or deposits of salts or the like, particularly when the primary medium is a coolant liquid which removes heat from the secondary medium surrounding the outsides of the tubes of the tube handle.

Fouling on the insides of the tubes of a heat exchanger is difficult to detect, and the degree of fouling is extremely difficult to measure, excepting that when there is inadequate heat exchange, the resulting trouble naturally leads to a suspicion that the heat exchanger tubes are fouled and possibly actually clogged Heretofore the practice has been to from time-to-time measure the thermal balance between the two mediums passing through the heat exchanger. Also it is, of course, possible to disassemble the heat exchanger for internal inspection of each tube of the tube bundle. Both expedients are time-consuming, put the heat exchanger out of operation, and are normally only resorted to when the heat exchanger fails to operate satisfactorily. Both expedients involve uncertainties and neither permits continuous monitoring of the heat exchanger's efficiency.

SUMMARY OF THE INVENTION

The purpose of the present invention is to provide an apparatus for continuously monitoring, and possibly actually measuring, the degree of fouling occurring inside of the heat-exchanger tubes while the heat exchanger continuously operates. Use of the apparatus makes it possible to anticipate the time when the heat exchanger must be taken out of operation for servicing or, possibly, for replacement, avoiding the use of the previously referred-to expedients which may possibly prove to be either premature or too late.

This new apparatus fundamentally is for measuring fouling on the inside of a heat-exchanger tube containing a fluid flow capable of fouling the tube's inside, with time. Normal tubular heat-exchanger constructions involve the use of tubes made of metal and having the same chemical compositions and heat treatment history, uniformly for all tubes of the tube bundle.

With the above in mind, the apparatus of the present invention comprising a test tube having substantially the same composition as any one of the heat-exchanger tubes, and preferably having the same diameter. This test tube should have a reasonably substantial length but it need not be as long as the heat-exchanger tubes. A portion of the flow of the primary medium through the heat exchanger is continuously shunted through this test tube, by means of appropriate piping, preferably at the same flow rate as the primary medium flows through the heat-exchanger tube bundle. A pressure chamber surrounds and encloses the outside of this test tube isolating the outside of this test tube from external uncontrollable influences. The pressure vessel is designed to form a space surrounding the test tube and the pressure chamber has means for filling this space with a vapor that condenses to liquid on the outside of the test tube, the vapor around the test tube being isolated from external influences.

With the shunted flow of primary medium flowing continuously through the apparatus during the continuous operation of the heat exchanger, the condensation of the vapor, and, therefore, the pressure within the pressure chamber, depends solely on the rate of heat exchange between the vapor and the primary medium flowing through the test tube of the apparatus. Therefore, by continuously measuring the internal fluid pressure within the pressure chamber, it is possible to continuously measure the rate of fouling inside of the test tube, and, since the test tube corresponds substantially exactly with the heat-exchanger tubes, the extent and rate of fouling within the heat-exchanger tubes is measured.

To keep the apparatus of the present invention compact, its test tube need not be made as long as the tubes of the heat exchanger, it being possible to make the exterior of the test tube finned to increase the rate of heat exchange between the vapor and the primary medium flowing through the test tube, whereby to compensate for any difference in length between the test tube and the heat-exchanger tubes.

The pressure chamber of this apparatus is necessarily elongated in the direction of the test pipe which the pressure chamber hermetically encloses. Preferably the apparatus is positioned horizontally, the pressure chamber being large enough to form an upper portion forming a vapor space around the test pipe, and a lower portion containing vaporizable liquid, such as water. With this arrangement, the water can be heated to form vapor in the vapor space which condenses on the test pipe's outside, assuming the primary medium passing through the heat exchanger, is a coolant With the above arrangement, the water used should be distilled water or, at least, water that cannot chemically or otherwise react with the outside of the test pipe. In other words, only the interior of the test pipe should be subjected to the fouling tendencies existing in the heat-exchanger tube. With this in mind, the pressure vessel can be externally heated via its bottom side, to thereby heat the liquid and its lower portion and provide the vapor surrounding the test pipe and which condenses on the outside of the test pipe more or less, dependent on the rate at which heat is abstracted from the vapor via the coolant, which is the same as the heat-exchanger coolant flowing through the inside of the exchanger.

For maximum accuracy of measurement, via measurement of the fluid pressure in the pressure chamber of this new apparatus, the heat supplied to the vaporizing liquid and the flow rate through the test pipe of the apparatus, should be held at constant values. This can be easily done reliably by using controlled electric heating of the liquid used to form the vapor and by the use of a constant delivery pump for feeding the heat exchanger's primary medium through the test tube of the apparatus. External heat loss can be reduced by thermally insulating the outside of the pressure chamber of the apparatus, although the use of a properly designed, externally finned test tube, permitting a short test tube length and, therefore, a short pressure chamber length, provides for measurement accuracy that is normally satisfactory.

BRIEF DESCRIPTION OF THE DRAWINGS

A specific example of the present invention is schematically illustrated by the accompanying drawings, in which.

DETAILED DESCRIPTION OF THE INVENTION

Figure 2:
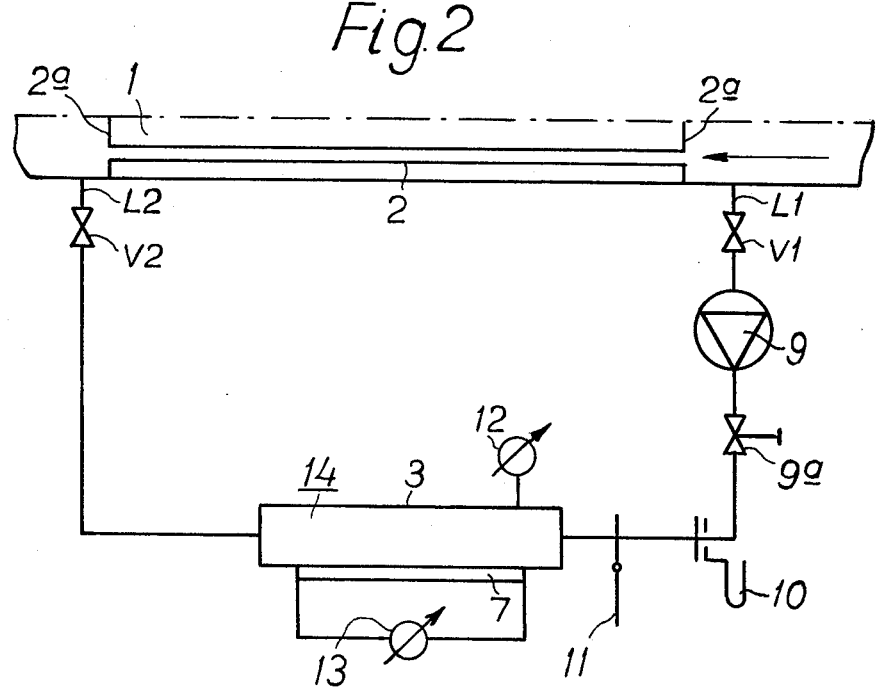
FIG. 2 is a flow diagram showing the apparatus in use.

Having reference to the above drawings, FIG. 2 schematically shows a tubular heat exchanger having a casing 1 forming a space for the secondary medium, communication being via the usual inlet and outlet connections (not shown), and one of the tubes 2 of the usual tube bundle, the tubes normally being mounted in tube sheets as indicated at 22. The flow of primary medium or coolant is indicated by the arrow in FIG. 2.

Figure 1:
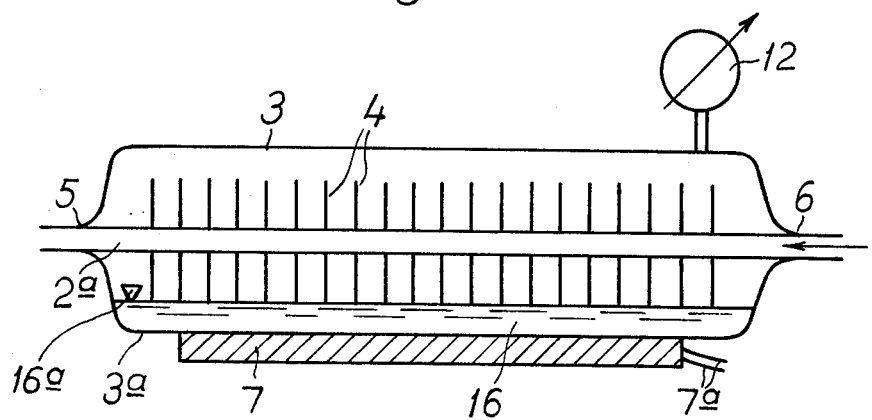
FIG. 1 is a vertical section.

The horizontally elongated pressure chamber of the new apparatus is shown at 3, as indicated in FIG. 1, in particular, this pressure chamber surrounding the test tube 2a externally having the fins 4 for increasing its external surface area and permitting the use of a relatively short test tube length, as contrasted to the length of the tube 2. Otherwise, the test tube 2a has the same metallurgical composition and treatment as the heat-exchanger tube 2. The pressure chamber casing 3 is hermetically welded to the test tube 2a at the locations 5 and 6 so that the test tube and its fins 4 are hermetically enclosed.

In this example, the lower portion 3a of the casing contains water as indicated at 16, the casing forming a vapor space surrounding the test tube 2a and its fins 4 above the water level indicated at 16a, this being the water level existing when the water 16 is unheated and the vapor space above the level 16a is free from vapor in the practical sense. The bottom of the casing 3a abuts an electric heater 7, its electric power lines being indicated at 7a. In this way the water 16 can be heated to fill the space within the pressure chamber and surrounding the test tube 2a and its fins 4 with water vapor.

As shown by FIG. 2, the apparatus of FIG. 1, here numeraled 14, is used in shunt with the heat exchanger. The primary medium is taken from the upstream one of the tube sheets 22 by a line L1 and is returned via a line L2 beyond the downstream one of the tube sheets 22. Valves V1 and V2 are provided for obvious reasons. The line L1 contains a pump 9 which provides for a constant flow rate to the apparatus 14, possibly under the influence of an adjustable valve 9a, monitored by a flow meter 10 and a temperature measuring device 11. The electric heater 7 is provided with a heat indicator 13. Thus, a constant flow input and a constant heat input to the apparatus 14, is made possible.

Measurement of the fluid pressure within the casing 3 of the apparatus is made possible by a fluid pressure indicator 12.

In use, assuming that the heat exchanger is in continuous operation with the primary medium, or coolant, flowing through all of its tubes, including the illustrated tube 2, the primary medium is continuously shunted via the lines L1 and L2, valves V1 and V2 being open, through the apparatus 14, and, therefore, through the test tube 2a. Using the heat indicator 13, the heat flow of the electric heater 7 is kept at a constant value heating the water 16 and surrounding the test tube and its fins 4, with the water vapor which is, of course, condensing, depending at the rate heat is removed from the water vapor via the primary medium or coolant feeding the tubes 2 and 2a. Assuming that the tubes 2 and 2a are new or just cleaned, a pressure value is obtained via the pressure indicator 12. The pump 9, possibly assisted by the valve 9a, both monitored by the flow meter 10, assure a constant flow through the test tube 2a. This control is considered advisable because in shunting the primary medium around the heat exchanger it would otherwise be possible for the flow rate through the test tube 2a to differ from the flow rate through the heat exchanger 2.

With continued operation and time, the heat-exchanger tube 2 begins to foul, and under the conditions referred to, the test tube 2a correspondingly fouls. With such fouling, the condensation of the vaporized liquid 16 decreases on the tube 2a and its fins 4 with the consequent increase of the pressure in the pressure vessel in order to keep the heatbalance, the pressure being measurable via the indicator 12. Assuming a constant flow rate and a constant heat input, the fluid pressure in the pressure chamber provides a reliable indication of measurement of the fouling occurring. If the temperature of the primary medium flowing through the heat exchanger varies, the temperature change is correspondingly reflected by the temperature measuring device 11 connected in the shunt pipe line loop including the new apparatus. Therefore, even in the event of such a variable, an accurate evaluation of the fouling is made possible by compensation for the effect of this variable on the pressure reading obtained via the pressure measuring device or gauge 12. Although not shown, gauges are commercially available having a movable scale, and when temperature changes are noted via the device 11, this scale can be adjusted accordingly so that always an accurate measurement of the fouling extent can be determined.

Although not shown, presently available automatic controls, compensation equipment and the like, can be used to make the new apparatus independent of human control. Instead of the water shown at 16, any other means can be used for surrounding the test tube with a condensable vapor, the condensation of which is a reflection of the heat conductivity of the test tube and resulting in corresponding pressure variations within the pressure vessel formed by the casing 3.

What is claimed is:

1. An apparatus for measuring fouling on the insides of the tubes of a working heat exchanger comprising a casing surrounding the tubes with the tubes internally carrying a flow of medium capable of fouling the tubes' insides; said apparatus being separate from said heat exchanger and operative without putting the heat exchanger out of operation and comprising a test tube having substantially the same composition as said heat exchanger tubes, conduit means for conducting a portion of said flow through said test tube, a pressure chamber surrounding and enclosing at least a portion of the outside of said test tube and forming a space therearound isolated from external uncontrollable influences, a condensible vapor contained by said chamber in said space, the total quantity of condensed and uncondensed vapor being constant and means for measuring the fluid pressure in said space as determined by the condensation of said vapor in the space.

2. The apparatus of claim 1 in which said portion of the test tube has attached external fins inside of said pressure chamber and in said space so that the heat exchanger rate of said portion is increased to a degree permitting said apparatus to be shortened as compared to the length that would be required in the absence of said fins for equal operative effectiveness.

3. The apparatus of claim 2 in which said test tube and pressure chamber are axially elongated and horizontally positioned and the chamber contains a liquid provided with heating means for forming said vapor.

4. The apparatus of claim 3 in which said conduit means is also for adjustably controlling the flow rate of said flow portion.

* * * * *